(12) United States Patent
Bhuyan et al.

(10) Patent No.: US 6,634,217 B1
(45) Date of Patent: Oct. 21, 2003

(54) LIVE LINE METHOD AND TOOL FOR IDENTIFYING ELECTRICAL CONDUCTORS

(75) Inventors: Gouri S. Bhuyan, North Delta (CA); Avaral S. Rao, Coquitlam (CA); Chien Kang Kung, Richmond (CA); Dexter G. Tarampi, Coquitlam (CA); Roy G. O'Hara, Victoria (CA)

(73) Assignees: British Columbia Hydro and Power Authority, Vancouver (CA); Powertech Labs Inc., Surrey (CA)

( * ) Notice: Subject to any disclaimer, the term of this patent is extended or adjusted under 35 U.S.C. 154(b) by 0 days.

(21) Appl. No.: 10/107,184

(22) Filed: Mar. 28, 2002

(51) Int. Cl.7 .............................. G01N 3/48; G01N 3/43
(52) U.S. Cl. ................................................. 73/81; 73/82
(58) Field of Search .................................. 73/78, 81, 82

(56) References Cited

U.S. PATENT DOCUMENTS

| 4,079,978 A | * | 3/1978 | McMullin ................. 294/19.1 |
| 4,535,623 A | * | 8/1985 | Gilberto ........................ 73/81 |
| 5,337,566 A | * | 8/1994 | Lomastro et al. ............. 227/10 |
| 5,341,088 A | * | 8/1994 | Davis ........................ 324/106 |
| 5,397,982 A | * | 3/1995 | Van Lankvelt .............. 324/126 |

* cited by examiner

Primary Examiner—Hezron Williams
(74) Attorney, Agent, or Firm—Oyen Wiggs Green & Mutala

(57) ABSTRACT

The present invention provides a method of live testing of the hardness of a target electrical distribution wire having a known gauge, and a tool for same, the method comprising: a) providing a hardness testing tool at the operating end of an insulated tool for manipulating live distribution lines, wherein the hardness testing tool comprises a testing surface of known hardness; b) forcing the testing surface against the target wire; and c) comparing the resultant degree of deformation or lack of deformation on the testing surface with the expected degree of deformation which would occur for wire of that gauge having a specific hardness.

15 Claims, 18 Drawing Sheets

_US 6,634,217 B1_

LIVE LINE METHOD AND TOOL FOR IDENTIFYING ELECTRICAL CONDUCTORS

TECHNICAL FIELD

The invention relates to tools for handling live electrical conductors, and more particularly to a method and tool for testing the hardness of a live electrical conductor.

BACKGROUND ART

Copper wire has been widely used in the past as the material of construction for electrical power distribution lines. Some distribution lines contain soft annealed copper wire, while others contain hard drawn or medium hard drawn copper wire. Hard drawn and medium hard drawn wire have a considerably higher minimum breaking strength than soft annealed wire. When soft annealed copper wire distribution lines are restrung due to aging, there is a risk of breakage and in-service failure.

In order to distinguish which distribution lines are made of hard drawn copper and which are made of soft annealed copper, hardness testing must be done. Since existing methods of hardness testing require that the power through the wire be shut down prior to testing, it has been considered more efficient to simply replace all the copper wire, whether hard, medium hard drawn or soft annealed, with aluminum conductors. This represents a considerable waste of perfectly serviceable wire. If the hard or medium hard drawn wire could be preserved by hardness testing without any power disruption, such blanket replacement programs could be avoided. What is needed is a method and tool for live testing of the hardness of distribution line copper conductors.

DISCLOSURE OF INVENTION

The present invention provides a method of live testing of the hardness of a target electrical distribution wire having a known gauge. The method comprises a) providing a hardness testing tool at the operating end of an insulated tool for manipulating live distribution lines, wherein the hardness testing tool comprises a testing surface of known hardness; b) forcing the testing surface against the target wire; and c) comparing the resultant degree of deformation or lack of deformation on the testing surface with the expected degree of deformation which would occur for wire of that gauge having a specific hardness.

The present invention further provides a tool for live testing of the hardness of a target electrical distribution wire having a known gauge. The tool comprises an elongated insulated handle and is provided at the operating end thereof with a hardness testing element, wherein the hardness testing element comprises a testing surface of known hardness, the hardness testing element being adapted to force the testing surface against the target wire.

BRIEF DESCRIPTION OF DRAWINGS

The drawings illustrate a preferred embodiment of the invention.

BEST MODE(S) FOR CARRYING OUT THE INVENTION

Figure 1:
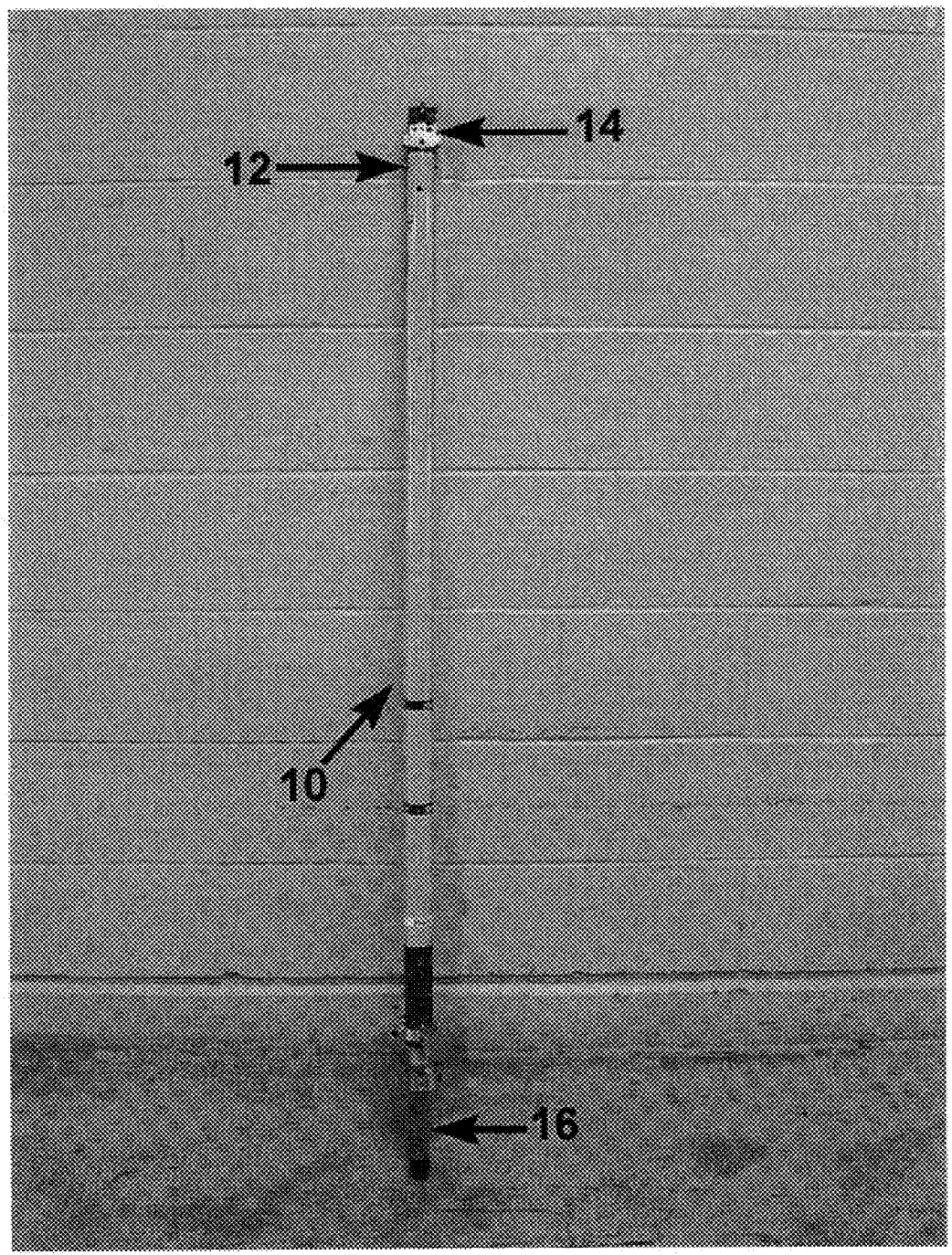
FIG. 1 is a perspective view of a tool according to the invention.

With reference to the drawings, the present invention 10 shown in FIG. 1 comprises a "hot stick" modified to allow hardness testing. Hot sticks are manufactured to allow workers to handle live electrical distribution lines without risk of electrocution. For example, they may be used when splicing or disconnecting live power lines.

Figure 2:
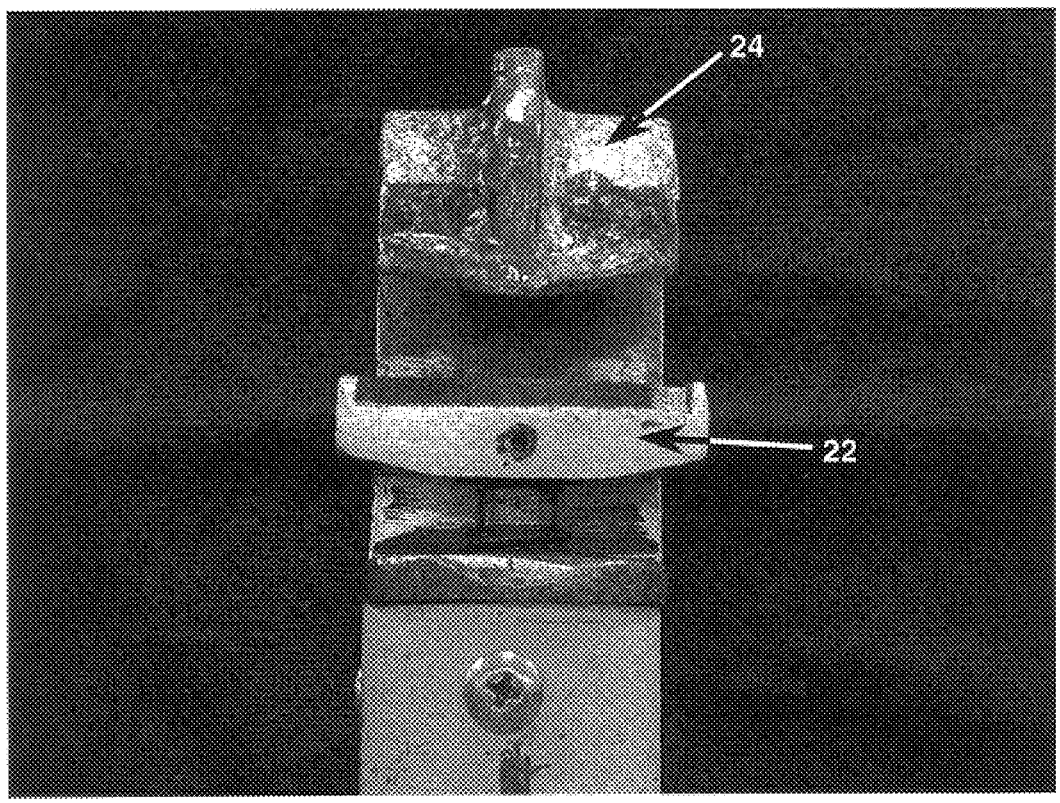
FIGS. 2 and 3 are front and side views respectively of the prior art tool head.
Figure 3:
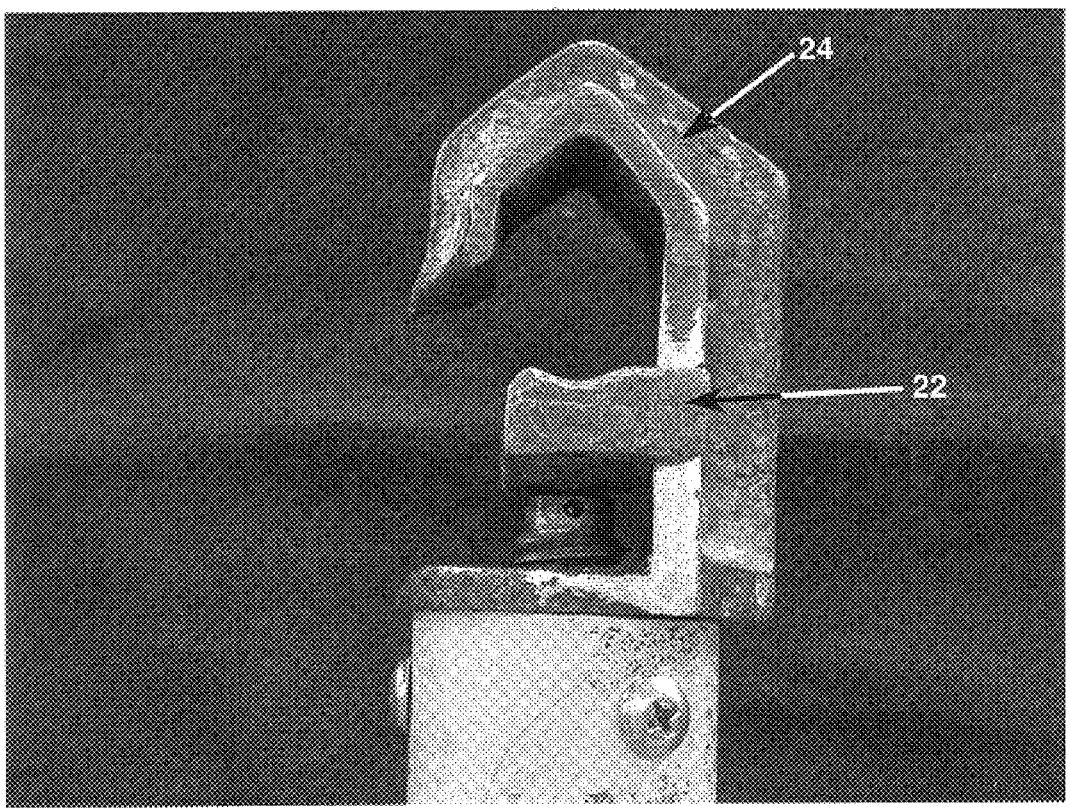
Figure 4:
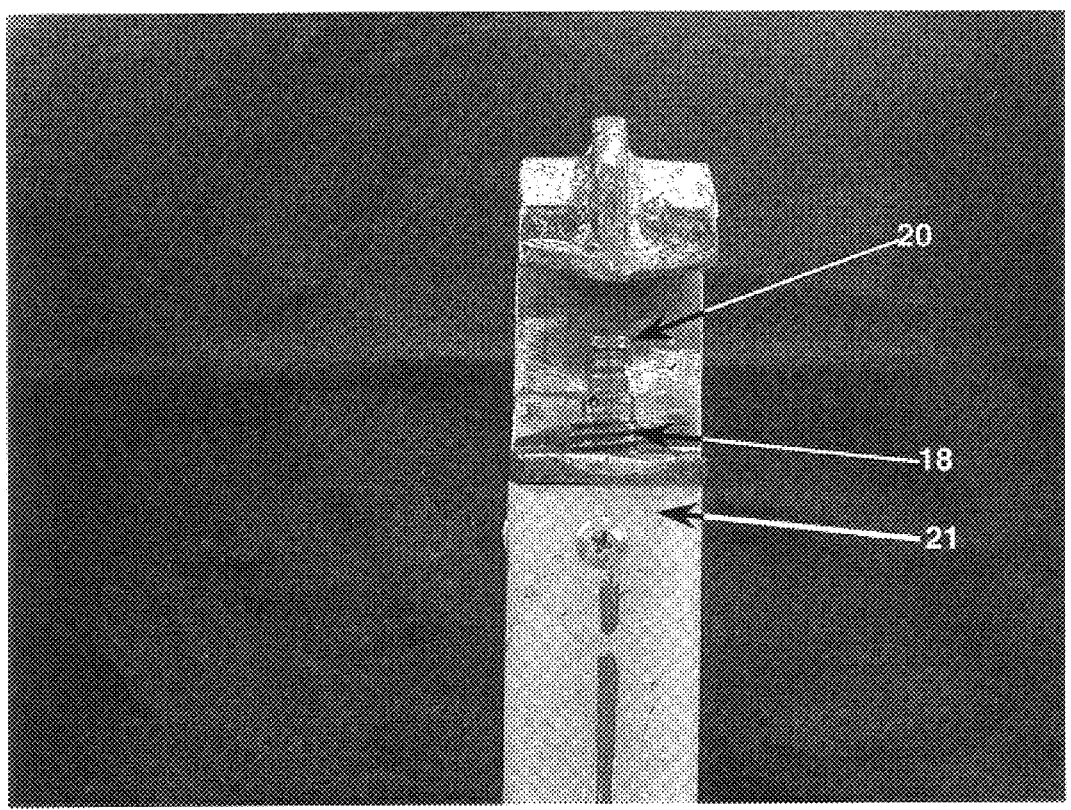
FIGS. 4 and 5 are front and side views respectively showing the upper screw threaded end of the prior art tool head shown in FIGS. 2 and 3.
Figure 5:
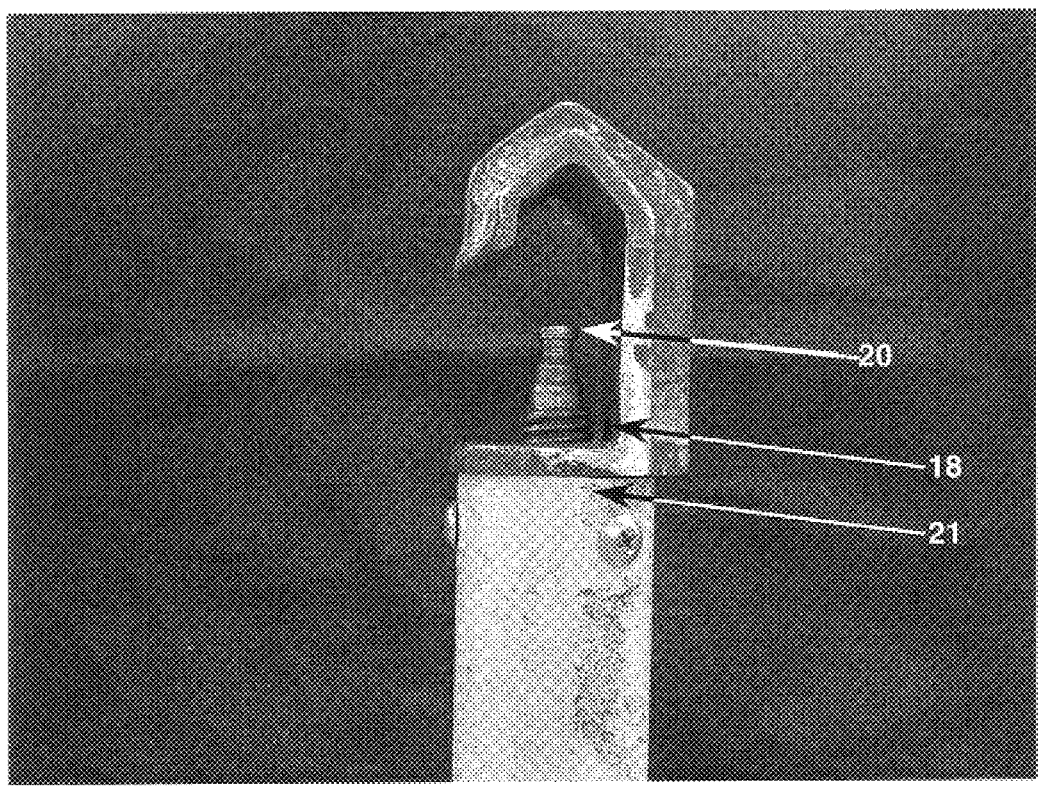
Figure 6:
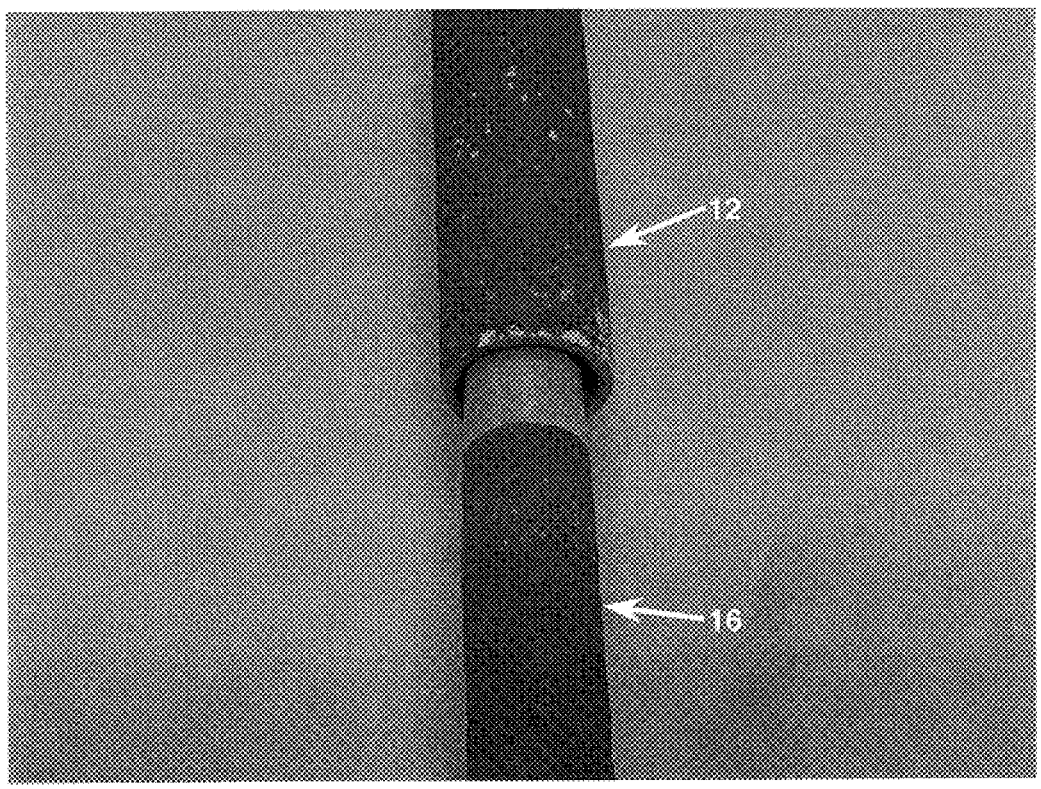
FIG. 6 is a partial perspective view of the nested rotatable inner pole of the tool shown in FIG. 1.
Figure 7:
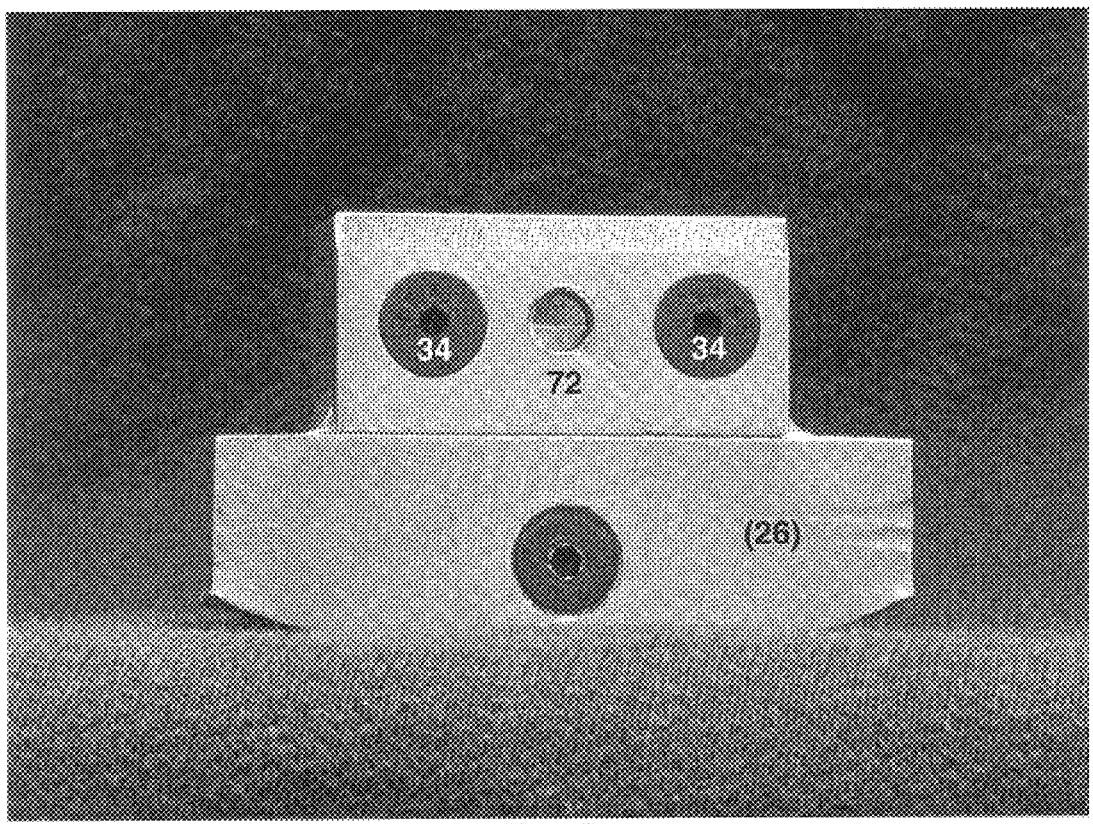
FIGS. 7 through 10 are front, side, top and bottom views respectively of the indentation block holder according to the invention with the indentation block removed.
Figure 8:
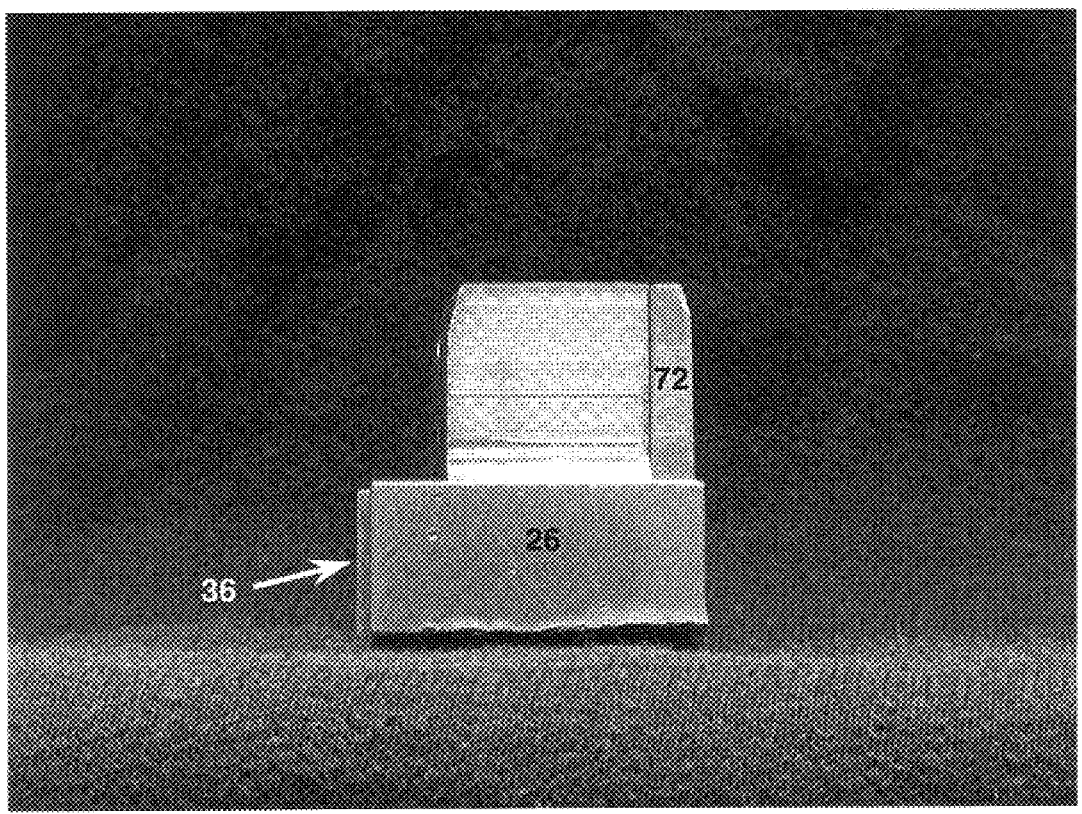
Figure 9:
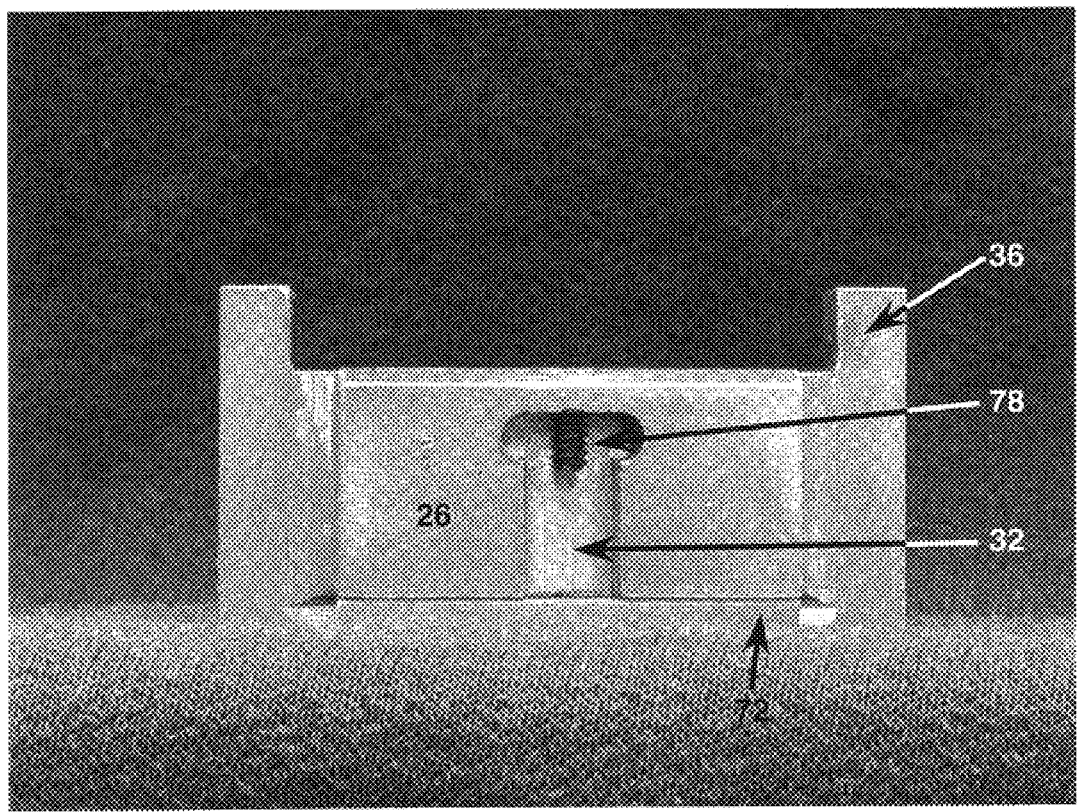
Figure 10:
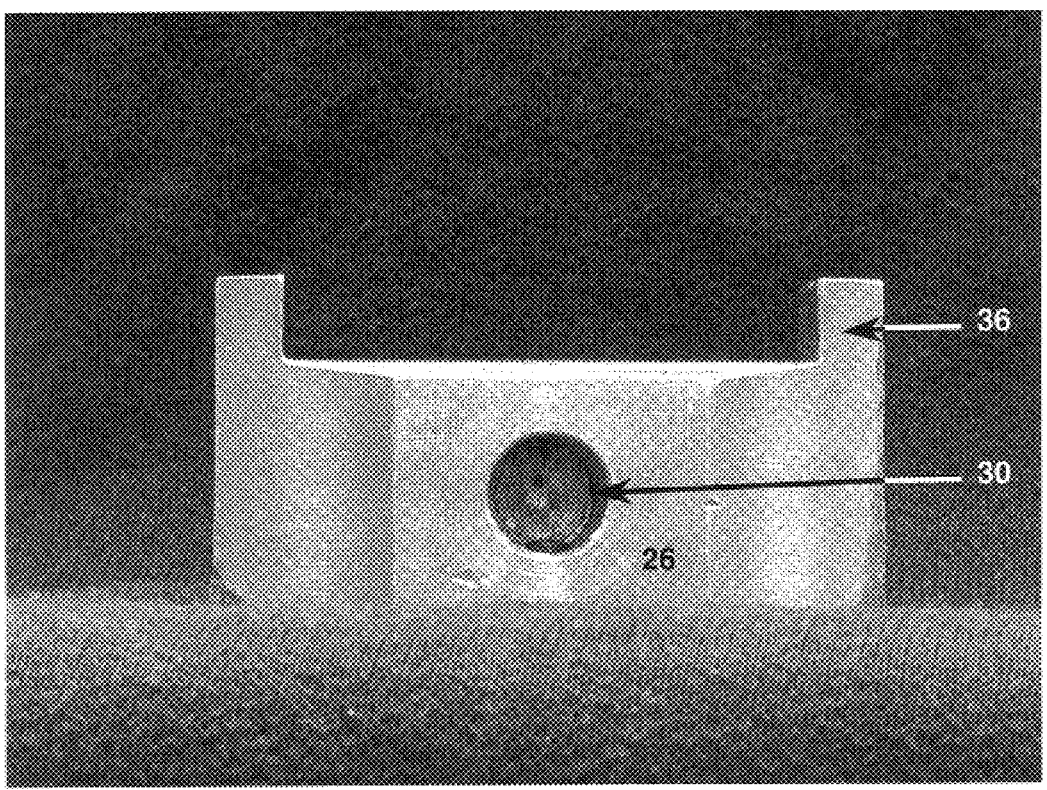

A hot stick modified according to the invention is shown in FIG. 1. As with current hot sticks, the invention comprises an elongated, insulated hollow cylindrical outer pole 12. It has a modified tool head 14 and a modified nested rotatable inner pole 16. The nested rotatable inner pole 16 prior to modification is shown in FIG. 6. It extends within, and is rotatable within, outer pole 12. It is connected to an upper screw threaded end 18, shown in FIGS. 4 and 5, which extends through a threaded nut (not shown) secured in the end 21 of outer pole 12 adjacent the tool head 14 whereby rotation of inner pole 16 causes the connector end 20 of threaded end 18 to extend from, or be drawn back towards, the end 21. Thus in the case of the prior art tool head, shown in FIGS. 2 and 3, a wire supporting piece 22 is rotatably connected to connector end 20 and can be moved towards or away from hook 24 to clamp the tool head to a wire, or release the tool head from the wire.

Figure 11:
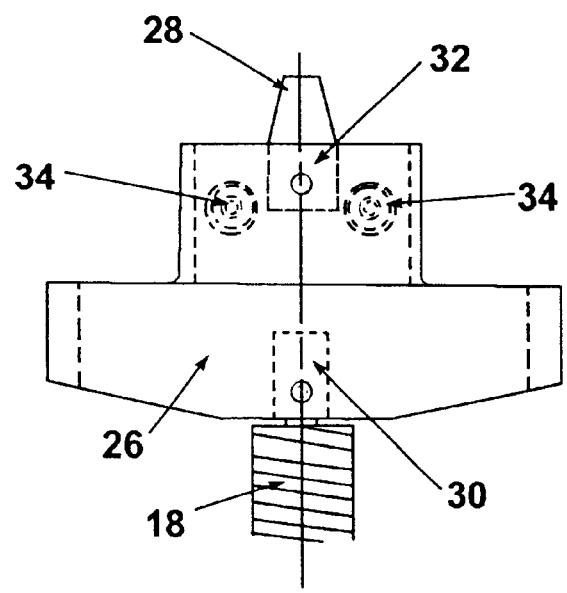
FIGS. 11 and 12 are front and side views respectively of the indentation block holder according to the invention with the indentation block in place.
Figure 12:
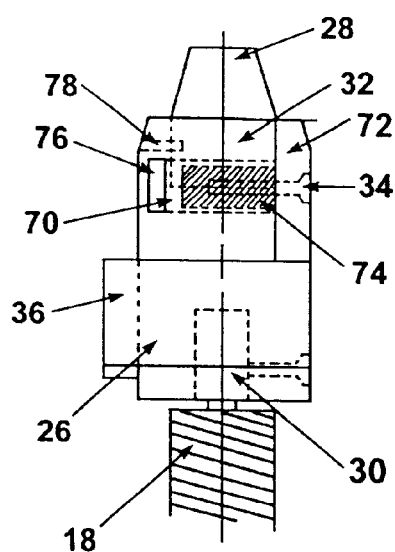
Figure 13:
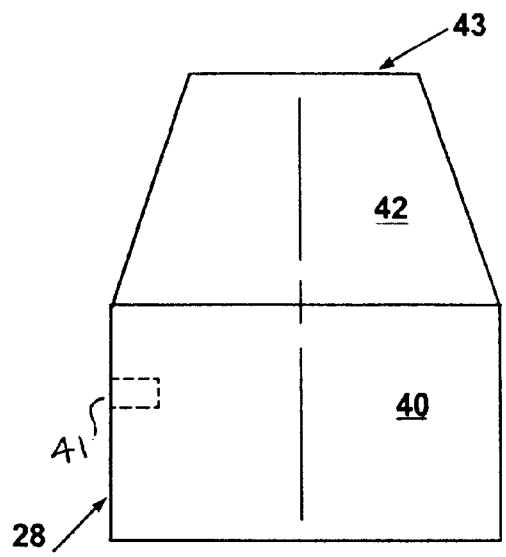
FIGS. 13 and 14 are front and side views respectively of the indentation block and test surface.
Figure 14:
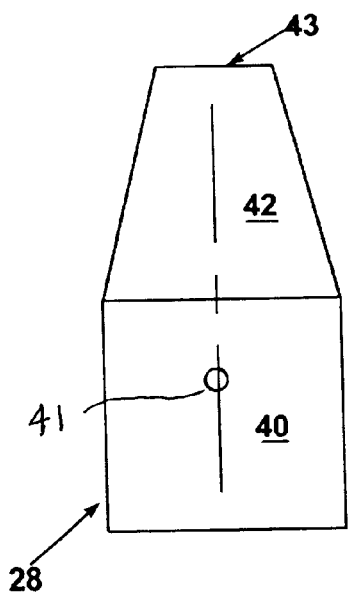

To manufacture the present invention, the tool head 14 is modified by replacing the existing wire supporting piece 22 with an indentation block holder 26, shown in FIGS. 7 through 12. The indentation block holder holds the indentation block 28 in place. It can be machined from a free cutting brass (C36000). The indentation block holder has three cylindrical cavities: cavity 30 for the receiving end 20 (FIG. 5) and two cavities 70 for two steel cylinders 74; and a rectangular cavity 32 for receiving the indentation block 28. Two magnets 76 are permanently embedded in cavities 70 as shown in FIG. 12. Screws 34, together with a faceplate 72, steel cylinders 74, magnets 76 and a set screw 78, hold the indentation block 28 in place. Steel cylinders 74 and magnets 76 assist in retaining indentation block 28 by magnetic attraction, while set screw 78 can be tightened against indentation block 28 to retain it. Arms 36 ensure that the holder moves in alignment with the tool head 14.

Indentation block 28 is shown in FIGS. 11, 12, 13, and 14. For purposes of distinguishing hard or medium hard drawn #6 copper wire from soft annealed #6 copper wire, it is made of a cartridge brass (C26000) that is 70% copper and 30% zinc, with a Rockwell "B" hardness value of 65±1.0. Testing for other types of wire of different hardnesses will require a different hardness/composition for the indentation block. The hardness of the block 28 is selected so that the target wire will be too soft to indent the upper surface of the block when forced against it, but the harder copper wire will cause an indentation. Thus it serves to differentiate wires of different hardnesses. It has a body portion 40 which typically forms a block about 0.25"×0.30"×0.50" and a tapered upper portion 42 with an upper planar surface 43, typically 0.30"× 0.16". Aperture 41 receives set screw 78.

Figure 15:
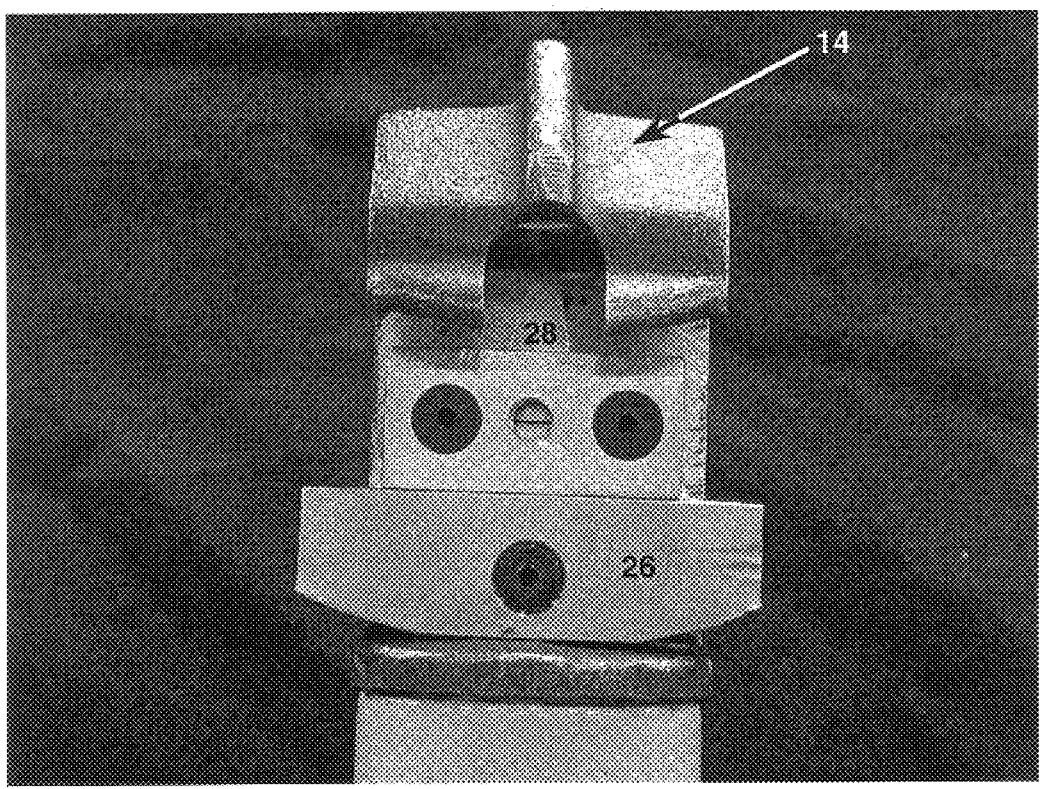
FIGS. 15 and 16 are front and side views respectively of the indentation block holder according to the invention with the indentation block in place installed in the tool head.
Figure 16:
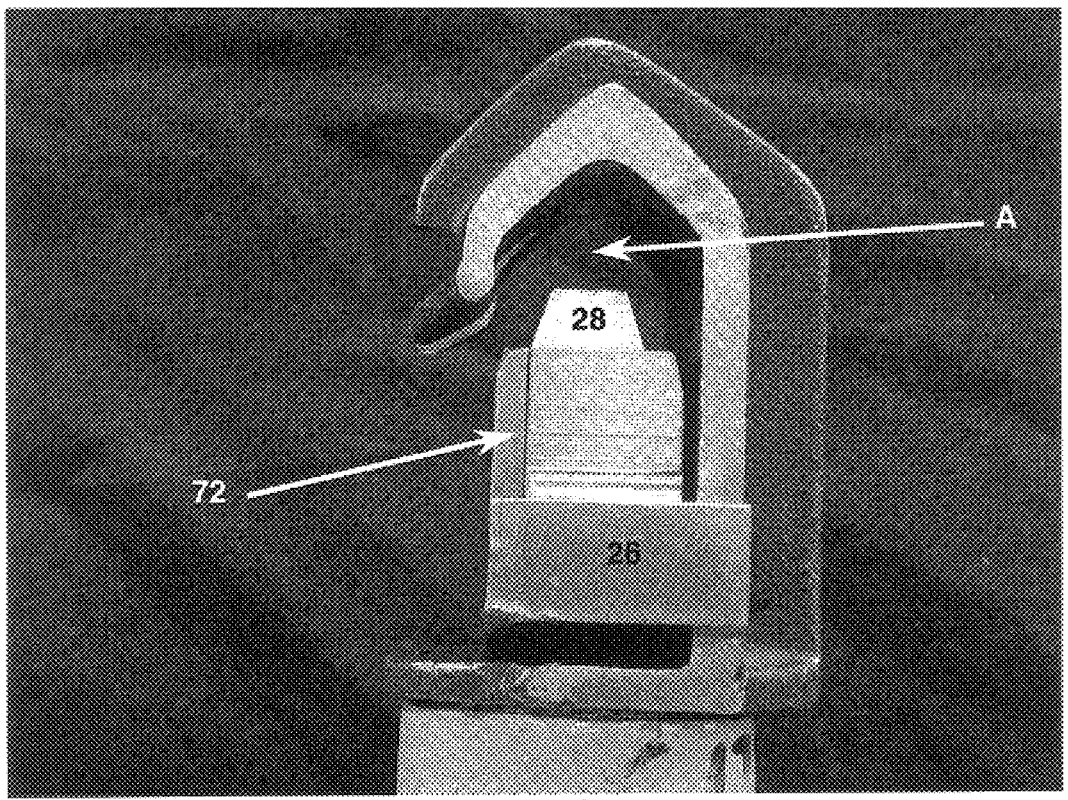

FIGS. 11 and 12 show the indentation block 28 seated in the holder 26. FIGS. 15 and 16 show the holder 26 with the indentation block 28 in place and fastened onto the head of the screw threaded end 18 in tool head 14. The block 28 is aligned to be perpendicular to the wire to be tested when held in tool head 14.

Figure 17:
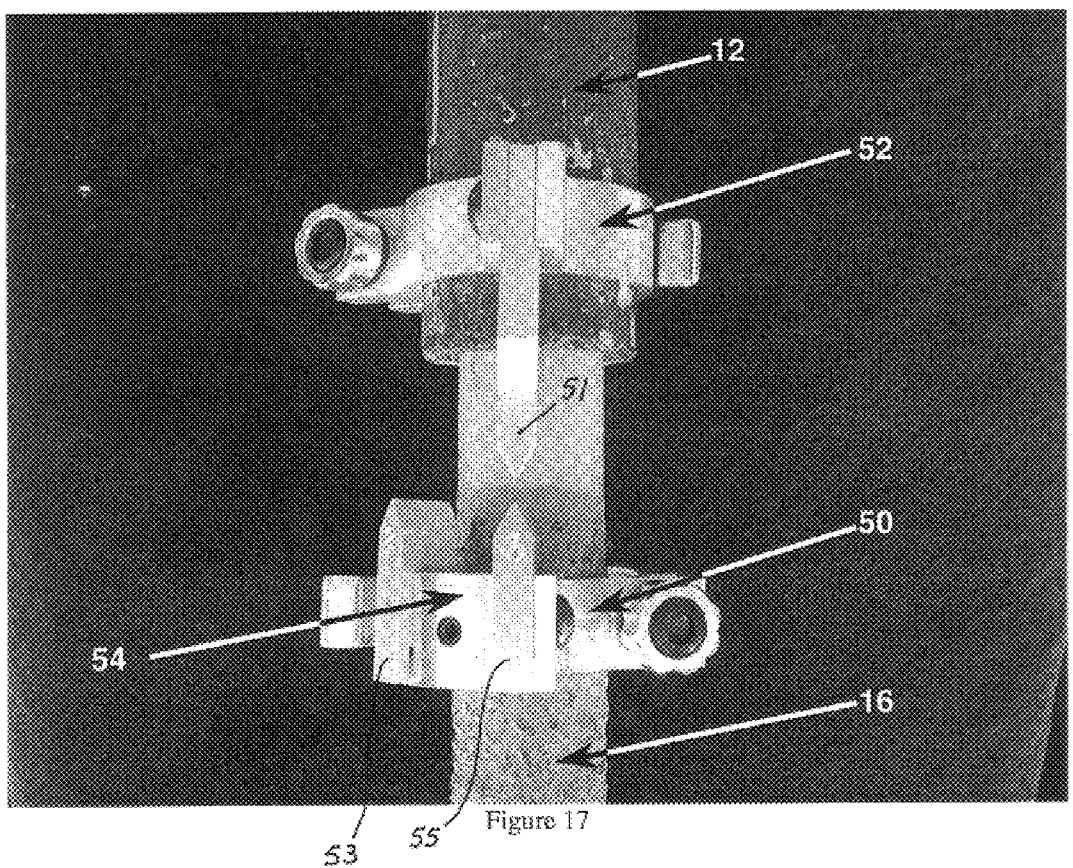
FIGS. 17 and 18 are partial perspective views illustrating the location of the load indicator and its arrangement with respect to the hot stick.
Figure 18:
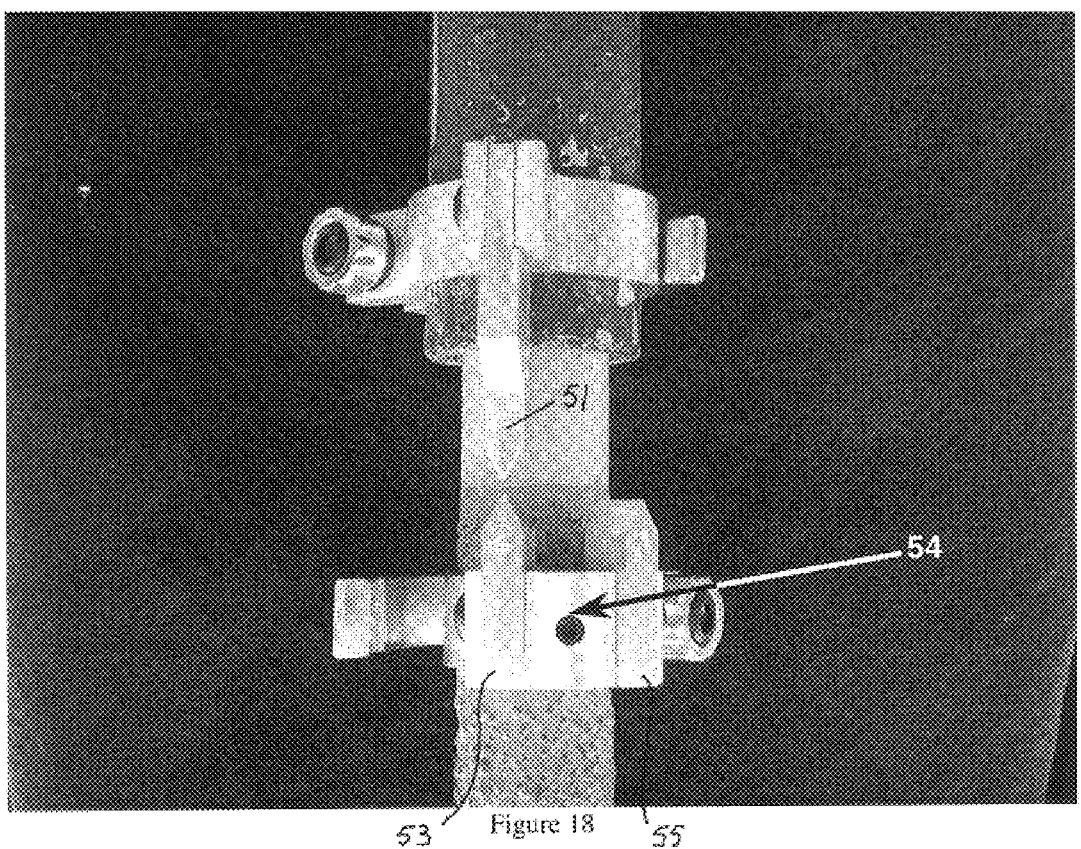

Load indicators are added to the bottom of the hot stick 10, shown in FIG. 1, to provide a pre-determined load as illustrated in FIGS. 17 and 18. The location of the indicators and their arrangement with respect to the hot stick are illustrated in FIGS. 17 and 18. FIG. 17 shows indicator elements 50 and 52, which form two separate lower and upper matching units fixed to inner pole 16 and outer pole 12, respectively. Element 50 rotates with pole 16 while element 52 is fixed to pole 12. Element 50 comprises a pointer 51 and element 52 comprises pointers 53, 55. The width of the separation 54, from 53 to 55, represents the rotative force needed to properly indent the indentation block. The indicator elements are made of aluminum alloy 6061-T6. The indicator controls the loading that is the expected contact force between the indentation block and the copper wire. It is important that the operator tighten the hot stick with a controlled force. Too much or too little force will produce an unexpected result.

Figure 19:
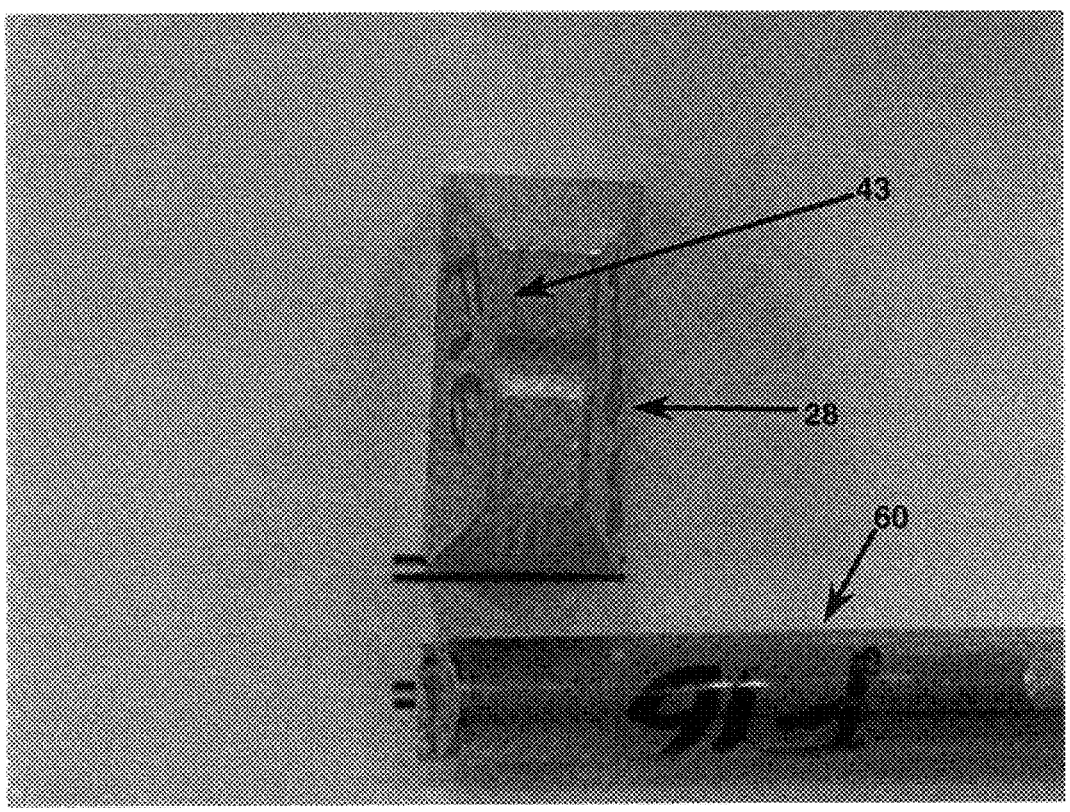
FIGS. 19 and 20, respectively, illustrate the surface of the indentation block after testing of medium hard drawn and soft annealed #6 copper wire.
Figure 20:
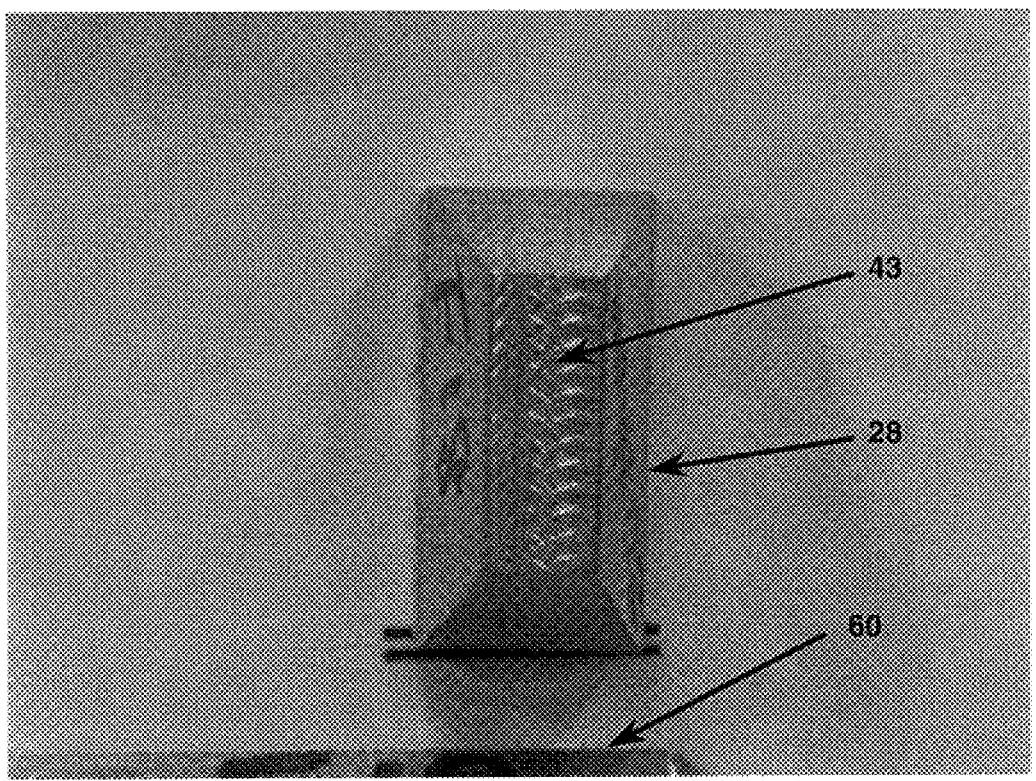

During operation, the head of tool 14 is placed over the bare, uninsulated wire to be tested 60 so that the wire extends through space A in FIG. 16. The inner pole is rotated clockwise until it reaches a position where the lower indicator 55 is in alignment with the upper pointer 51 as shown in FIG. 17. The operator then rotates the inner pole farther, tightening the indentation block 28 against the test wire until the lower indicator 53 is in alignment with the upper pointer 51, as shown in FIG. 18. The inner pole is then loosened and the hot stick is removed from the test wire. The surface 43 of the indentation block 28 is examined. If it displays a significant indentation from the wire, as in FIG. 19, then the wire is hard or medium hard drawn and need not be replaced. If it does not display a significant indentation from the wire, as in FIG. 20, then the wire is soft annealed and requires replacement.

Many alterations and modifications are possible in the practice of this invention without departing from the spirit or scope thereof. Accordingly, the scope of the invention is to be construed in accordance with the substance defined by the following claims.

What is claimed is:

1. A method of live testing of the hardness of a target electrical distribution wire having a known gauge, comprising:
   a) providing a hardness testing tool at the operating end of an insulated tool for manipulating live distribution lines, wherein said hardness testing tool comprises a testing surface of known hardness;
   b) forcing said testing surface against said target wire; and
   c) comparing the resultant degree of deformation or lack of deformation on said testing surface with the expected degree of deformation which would occur for wire of said gauge of a specific hardness.

2. The method of claim 1 wherein said testing surface is forced against said target wire by applying a pre-determined amount of force.

3. The method of claim 1 wherein said testing surface is forced against said target wire by advancing said testing surface against said target wire through a pre-determined distance.

4. The method of claim 3 wherein said insulated tool comprises an elongated insulated handle provided with a wire-retaining element for receiving said target, said elongated handle comprises inner and outer nested elements and said testing surface is advanced by rotating said inner element relative to said outer element.

5. A tool for live testing of the hardness of a target electrical distribution wire having a known gauge, comprising an elongated insulated handle and provided at the operating end thereof with a hardness testing element, wherein said hardness testing element comprises a testing surface of known hardness, said hardness testing element being adapted to force said testing surface against said target wire.

6. The tool of claim 5 wherein said tool is provided with a wire-retaining element for receiving said target wire and means for advancing said testing surface into contact with said target wire when in said wire-retaining element.

7. The tool of claim 6 wherein said means for advancing said testing into contact with said target wire when in said wire retaining element comprises a screw-threaded end secured to said hardness testing tool which is advanced and retracted by rotation thereof.

8. The tool of claim 6 wherein said means for advancing said testing surface into contact with said target wire when in said wire retaining element further comprises means to prevent the advancing of said screw-threaded end beyond a pre-determined maximum.

9. The tool of claim 5 wherein said hardness testing element comprises a metal element of known hardness having a surface adapted for contacting said target wire.

10. The tool of claim 5 wherein said elongated handle comprise inner and outer nested elements and said screw-threaded end is secured to said inner element.

11. The tool of claim 9 wherein said metal element is removably secured in said hardness testing element.

12. The tool of claim 9 wherein said metal element is removably secured in said hardness testing element by screw means.

13. The tool of claim 9 wherein said metal element is removably secured in said hardness testing element by magnetic means.

14. The tool of claim 8 wherein said metal element is made of brass.

15. The tool of claim 9 wherein the hardness of said metal element is selected so that certain types of target wire will be too soft to indent the surface of said metal element when forced against it, but other types of target wire will cause an indentation.

* * * * *